United States Patent
de Meijer

(10) Patent No.: US 7,235,780 B2
(45) Date of Patent: Jun. 26, 2007

(54) METHOD AND SYSTEM FOR DETECTING A PROPERTY OF A PAVEMENT BY MEASURING GAMMA-RADIATION

(75) Inventor: Robert Johan de Meijer, Peize (NL)

(73) Assignee: Rijksuniversiteit Groningen, Gronigen (NL)

( * ) Notice: Subject to any disclaimer, the term of this patent is extended or adjusted under 35 U.S.C. 154(b) by 0 days.

(21) Appl. No.: 10/511,995

(22) PCT Filed: Apr. 28, 2003

(86) PCT No.: PCT/NL03/00313

§ 371 (c)(1),
(2), (4) Date: Aug. 15, 2005

(87) PCT Pub. No.: WO03/091726

PCT Pub. Date: Nov. 6, 2003

(65) Prior Publication Data

US 2006/0000972 A1    Jan. 5, 2006

(30) Foreign Application Priority Data

Apr. 26, 2002    (EP) .................................. 02076684

(51) Int. Cl.
*G01N 23/00*    (2006.01)
(52) U.S. Cl. ..................................... 250/253
(58) Field of Classification Search ................ 250/255, 250/491.1, 253
See application file for complete search history.

(56) References Cited

U.S. PATENT DOCUMENTS 4,089,054 A    5/1978 Ott (Continued)

FOREIGN PATENT DOCUMENTS

| GB | 1 179 172 A | 1/1970 |
|---|---|---|
| WO | 02 03055 A | 1/2002 |

OTHER PUBLICATIONS

Hendricks, et al., "Full-spectrum analysis of natural gamma-ray spectra", Journal of Environmental Radioactivity, 2001, Elsevier, UK, vol. 53, No. 3, pp. 365-380.

(Continued)

*Primary Examiner*—David Porta
*Assistant Examiner*—Mark R. Gaworecki
(74) *Attorney, Agent, or Firm*—Pearne & Gordon LLP

(57) ABSTRACT

For detecting a property of at least one layer (301) of a pavement (300), a flux of radiation of energy levels or at least one range selected from an energy spectrum received from the pavement is measured in a position above the pavement. The measured radiation includes g-radiation emitted by at least one radionuclide in or under the pavement. Information regarding the property is determined from the measured flux and a relationship between at least one flux of g-radiation of the energy levels or the range or ranges selected from the energy spectrum and the property. Pavement layers typically contain different concentrations of g-radiation emitting radio nuclides than the roadbed or the soil underneath and this also applies to layers of pavement of different material compositions. Selectively processing measured radiation at different energy levels or in at least one selected energy range allows to determine information regarding properties of the pavement from measured g-radiation intensity more accurately.

17 Claims, 2 Drawing Sheets

U.S. PATENT DOCUMENTS

| | | | |
|---|---|---|---|
| 4,525,854 A | | 6/1985 | Molbert et al. |
| 5,025,150 A | * | 6/1991 | Oldham et al. ............. 250/253 |
| 5,029,194 A | * | 7/1991 | Young et al. ................. 378/89 |
| 5,412,206 A | * | 5/1995 | Seidel et al. ................ 250/253 |

OTHER PUBLICATIONS

Database WPI, Section PQ, Week 199146, Derwent Publications Ltd., London, GB; Class Q41, AN 1991-338269 XP002216256 & SU 1 617 078 A (UNIV KHARK), Dec. 30 1990 cited in the application abstract.

* cited by examiner

METHOD AND SYSTEM FOR DETECTING A PROPERTY OF A PAVEMENT BY MEASURING GAMMA-RADIATION

FIELD AND BACKGROUND OF THE INVENTION

The invention relates to a method for detecting a property of at least one layer of a pavement, to a system for carrying out such a method and to a computer program for use in such a method.

It is known from practice, to measure physical parameters of a pavement with ground radar. In this known method, radar waves are emitted by a radar source. The radar waves are partially reflected by the pavement and detected. The properties of the reflected radar waves may then be related to physical parameters of the pavement. For example, the intensity or the phase delay of the reflected radar waves is a measure for the thickness of the pavement.

However, a disadvantage of this known method is its complexity because a radar source and detector are required. Furthermore, it is difficult to identify a boundary between layers having approximately the same density and the emission and detection of radar waves may interfere with and be interfered by other applications involving the use of radar signals, such as navigation and traffic control.

From Soviet patent application 1 617 078 it is known to measure the intensity of γ-radiation before and after the application of a dressing layer and to use the difference between the measured total gamma ray intensities to assess the quality of the layer. However, the accuracy of such measurements is quite unreliable.

SUMMARY OF THE INVENTION

It is an object of the invention to provide a reliable solution for non-destructive determination of a property of at least one layer of a pavement.

According to the present invention, this object is achieved by carrying out a method for detecting a property of at least one layer of a pavement in accordance with claim 1. Also according to the invention, a system according to claim 10 for carrying out such a method as well as a computer system according to claim 11 and a computer program according to claim 12 for processing radiation measurement data in such a method are provided.

The measurement is reliable because it is hardly influenced by external influences. By specifically measuring and processing γ-radiation of various energy levels or at least one energy range, a more reliable and accurate determination of the property to be determined can be achieved, because the γ-radiation can be processed in accordance with energy levels and ranges tailored to the γ-radiation spectra and differences between γ-radiation spectra of the compounds of the pavement layer or layers and of the road bed and the ground underneath as well as to the properties to be monitored.

Specific embodiments of the invention are set forth in the dependent claims.

Further features, effects and details of the invention are described below with reference to the figures in the attached drawing.

DETAILED DESCRIPTION

Figure 1:
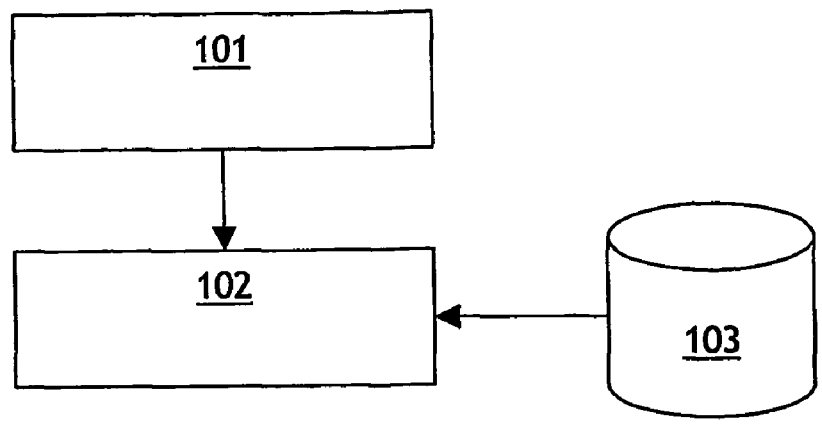
FIG. 1 is a flow-chart of a method according to the invention.

In the example of a method according to the invention shown in FIG. 1, in step 101 a flux of γ-radiation received from a road surface is measured. The flux, which may also be expressed in terms of the intensity of the radiation or the amount of radiation received over a period of time, can be determined for radiation emitted by a single radionuclide (for instance $^{40}$K, $^{232}$Th, $^{238}$U or the products of their radioactive decay) or for radiation emitted by several radionuclides. Which method is to be preferred depends on the composition of the pavement layer or layers and of the roadbed and on the property or properties to be measured. In step 102, a property of the pavement is determined from the measured flux or fluxes and data on the relation between the measured flux or fluxes and the property to be determined. The data on the relationship between measured flux and the property of the pavement layer to be determined, such as the materials used in the pavement or the thickness of (layers in) the pavement are obtained from a data store 103, for instance a computerized record such as a database. The steps 101, 102, 103 are separate steps, which may be carried out, in a single integrated apparatus. It is also possible to first collect radiation measurement data and to subsequently process these data in a separate data processor. Preferably, the radiation measurement data are associated to positional data. For calibrating the measurement results, use can also be made of calibration measurement results obtained from calibration samples physically extracted from the pavement, which calibration measurement results are preferably also associated to positional data and matched to radiation measurement data associated to the same positional data.

The γ-radiation received from the pavement can be composed of γ-radiation emitted by radionuclides in the pavement, radionuclides in the roadbed (and/or in the soil) underneath the pavement or both. Thus, emission of radiation to the pavement is not required.

In general, the concentrations of radio nuclides in a pavement layer are substantially different from the concentrations of radio nuclides in other layers which may include a layer or layers of the pavement, the roadbed and the soil under the pavement. Moreover, each layer absorbs γ-radiation and each layer located above another layer absorbs γ-radiation from the layer or layers underneath as well. The flux of γ-radiation received from the pavement by the detector is determined by the composition of the layers of the pavement, the roadbed and/or the soil underneath the pavement, the thickness or mass per unit of surface of the layers and the positions in vertical sense of the layers relative to each other.

More specifically, the thickness of a layer influences the flux of γ-radiation in two opposite ways: the thicker the layer, the more γ-radiation is emitted from the layer, but the more γ-radiation originating from layers underneath is extinguished. Depending on the composition of the pavement, γ-radiation contributions significant for the determination of the thickness of at least the topmost layer can be detected from as deep as 20 to 50 cm below the top surface of the pavement.

A pavement may consist of one or more distinguishable layers of different material compositions, each containing different concentrations of radionuclides. From detected γ-radiation which includes contributions from the radionuclides in a plurality of layers and which is also determined by extinction in the layers, the thickness of several layers can be estimated by measurement at energy levels or energy level ranges characteristic for a plurality of radionuclides.

In almost all earth materials, (small) amounts of natural radionuclides are present, such as $^{40}$K, $^{232}$Th, $^{238}$U and the products of their radioactive decay. Some of these radionuclides emit electromagnetic γ-rays. The concentration of the radionuclides depends on, inter alia, the type of material, the origin of the material and the treatment of the material. For example, sand has a two to five times lower concentration of Th and U than clay. Thus, the specific mixture of the radioactive decay products is unique for each material. Hence, the composition of the pavement may be determined by measuring the radiation from the pavement and comparing the measured radiation with predetermined references or 'fingerprints' of the constituents of the pavement composition. The composition of the pavement may also be determined by comparing the measured radiation directly with reference data for different compositions.

For detecting the γ-radiation, various types of detectors can be used. In one type of detector, the radiation to be detected is allowed to fall on a crystal, which generates a light flash in reaction. A single photon may cause such a light flash. These light flashes may then be applied to a photo multiplier or photodiode which converts the light flashes into electrical pulses. The number of pulses per unit time is a measure for the flux of the radiation while the height of each electrical pulse is a measure for the energy of the photon incident on the crystal. By counting the number of pulses for a period (for instance one to ten seconds) and sorting them according to pulse height, an energy spectrum can be composed, i.e. the number of photons recorded per unit time as a function of their energy.

Such a spectrum will contain peaks or lines, which are respectively caused at least substantially by the radionuclides mentioned. A peak or a set of peaks can then be ascribed to a nuclide. In addition, contributions from other physical phenomena are present in the spectrum, such as for instance the Compton effect. Nevertheless, the shape of the spectrum (i.e. the positions of the peaks and the Compton continuum) is characteristic for a given detector-pavement layer combination.

Figure 2:
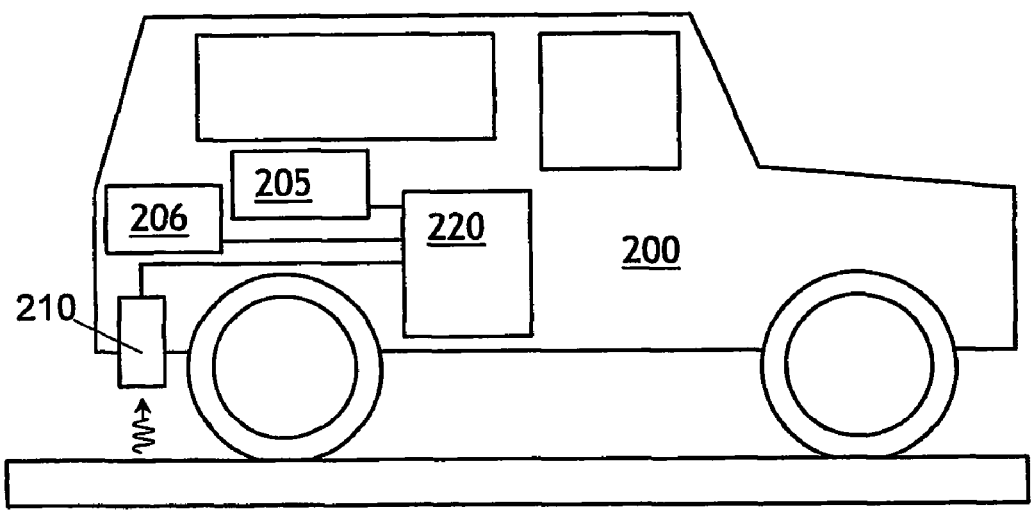
FIG. 2 schematically shows a vehicle provided with a system according to the invention, FIG. 3 schematically shows a cross-sectional view of a pavement, FIG. 4 schematically shows the radiation flux of the pavement of FIG. 3.
Figure 5:
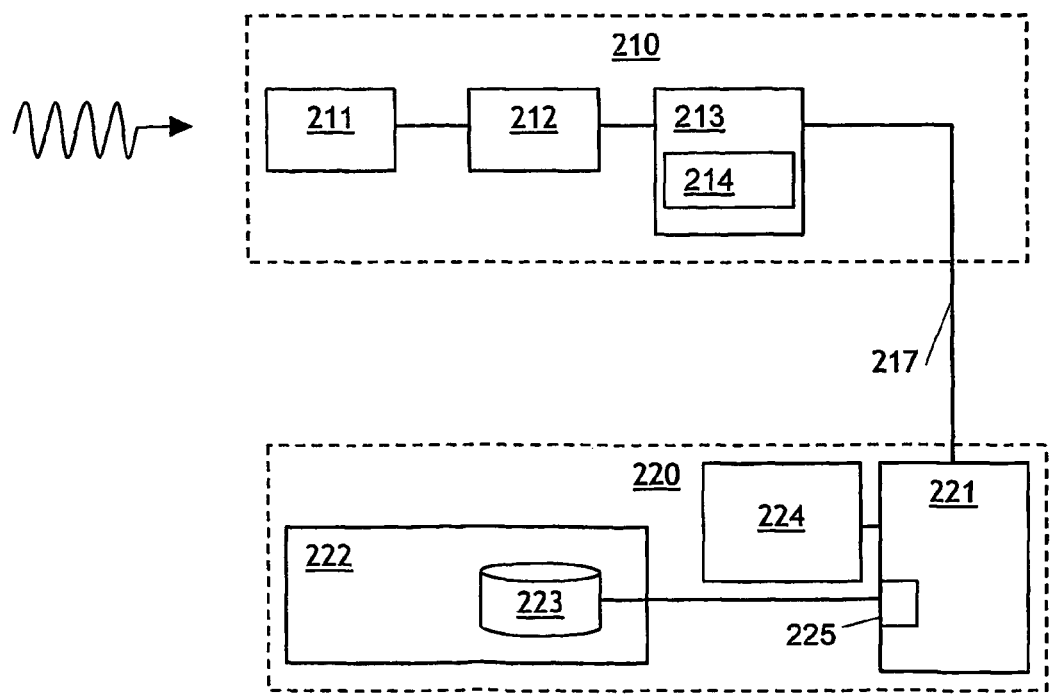
FIG. 5 shows a block diagram of a system according to the invention.

The vehicle 200 shown in FIG. 2 is provided with a system according to the invention, a position determining system 205 and may also be provided with other sensors known per se, such as sensors 206 for measuring unevenness of the road. The system comprises a γ-radiation detector 210 for measuring radiation received from below. Preferably, a plurality of detectors 210 is used so that a road can be scanned simultaneously along several scanning tracks laterally spaced from each other. The detectors can be shielded so that each detector receives γ-radiation from a limited range of directions only, for instance from a predetermined solid angle or from a predetermined detection window on the pavement which moves along the track to be scanned. The position determining system 205 and the detector 210 are communicatively connected to a computer system 220. As is shown in FIG. 5, the computer system 220 includes a processor 221 arranged to determine the property to be determined from the measured radiation and the data on the relation between radiation and the property to be determined stored in a memory 222. More specifically, the processor 221 may for instance be programmed to build up a γ-radiation spectrum over a preset time. The data regarding the measured γ-radiation and other measurement results are stored in a memory 222 in association with the position data from the position determining system 205 for on-line and off-line analysis. In such analysis, radionuclide concentrations or contributions from one or more radionuclides may first be calculated. It is also possible to directly compare the spectra with predetermined spectra corresponding to known pavement constructions. The computer also includes an interface 224 in the form of a display for signalling the results, such as the value of the determined property, and/or the quality of the analysis to the user.

As is shown in FIG. 5, according to the present example the detector 210 comprises a scintillation detector 211, known per se. The detector comprises a crystal that generates light flashes when photons of the radiation hit the crystal. The light flashes are converted to electrical pulses by a photo multiplier unit 212. The amplitude of the electrical signals is a measure for the energy of the γ-radiation that has hit the crystal.

The electrical signal is transmitted to a computer unit 213 in which the electric signal is digitized and subsequently aggregated in a digital data set representing a spectrum. Each time a preset time-interval has elapsed, the spectrum and associated positional data are stored in a memory 214 of the computer unit 213. According to the present example, the spectrum is subsequently analyzed in terms of radionuclide contribution data by using full spectrum analysis. For further details regarding full spectrum analysis, reference is made to "Full-Spectrum analysis of natural γ-ray spectra"; P. H. G. M. Hendriks, J. Limburg, R. J. de Meijer; *Journal of Environmental Radioactivity* 53 (2001), pages 365–380. On a display, the values of the radionuclide contribution data and positional data associated to the trajectory from which the measurements have been taken are displayed.

According to the present example, the desired information on the composition of the pavement is obtained via off-line analysis. The obtained radionuclide contribution data are transmitted to the computer unit 220 via data bus 217. In the computer 220, the radionuclide contribution data are corrected for the pavement conditions (such as composition and thickness of layers underneath). The corrected radionuclide contribution data are then converted to pavement build-up data using an algorithm containing the radionuclide contributions of the compositions constituting the pavement build-up. These concentrations have been determined beforehand in a separate laboratory analysis and stored in a database 223 in the memory 222 and can be inputted via interface 225. The stored radionuclide contributions may for instance be associated with materials for example in accordance with concentrations of K, U and Th and radioactive decay products of U and Th in those materials.

Figure 3:
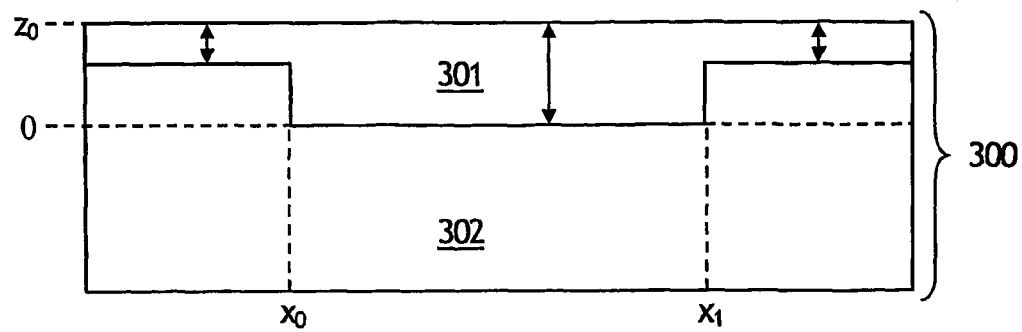
Figure 4:
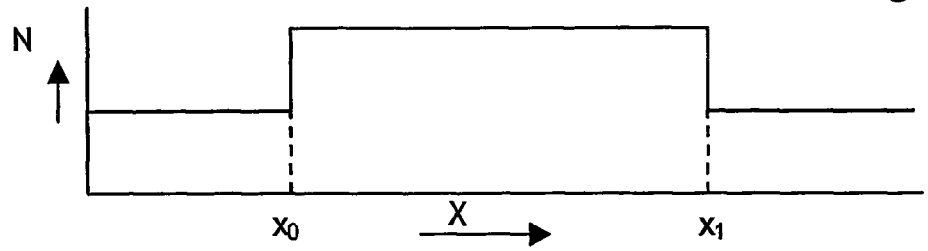

The radiation can also be used to determine the thickness of one or more layers of the pavement. In FIGS. 3 and 4, a pavement 300 having a single layer 301 is shown. The layer 301, which may for instance include bituminous, concrete or gravel material or shells, lies on top of a bed 302. The pavement layer 301 and the bed 302 each contain concentrations of natural radionuclei that emit γ-radiation with energy $E_\gamma$. The concentration of a particular radio nuclide in the pavement layer 301 is $C_1$. The concentration of that nuclide in the bed 302 is $C_2$. The thickness $z_0$ of the top-layer is to be determined. The bed 302 has a thickness beyond a depth from which significant amounts of γ-radiation are received and is therefore assumed to have a virtually infinite thickness.

Supposing an ideal situation in which the γ-radiation detector 201 is placed on a homogenous semi-infinitely extending layer. The γ-radiation flux towards the detector due to radionuclides with concentration $C_1$ in a layer of thickness dz is $N_1 dz$. Due to absorption of photons by material with thickness $z_z$ between the layer of thickness dz and the detector, the detector will detect a flux N of photons, which is equal to:

$$N_{dz} = N_1 e^{-\mu_1 \rho_1 z} dz \qquad (1)$$

In equation (1), μ represents the mass-attenuation coefficient and $\rho_1$ the bulk density of the material the pavement layer 301 is made of. For the top-layer 301 with thickness $z_0$, the flux of γ-radiation from the top-layer received by the detector in an ideal situation is:

$$N_1^{tot}(E_\gamma) = \int_0^{z_0} N_1 e^{-\mu_1 \rho_1 z} dz = \frac{N_1}{\mu_1 \rho_1}(1 - e^{-\mu_1 \rho_1 z_0}) \qquad (2)$$

The radiation flux resulting from the concentration $C_2$ in the ground-layer 302 at the transition between the top and ground layer is equal to:

$$N_2(E_\gamma) = \int_0^\infty N_2 e^{-\mu_2 \rho_2 z} dz = \frac{N_2}{\mu_2 \rho_2} \qquad (3)$$

The radiation from the ground-layer is partially absorbed by the top-layer. The flux of radiation from the ground layer 302, which reaches the detector, is therefore equal to:

$$N_2^{tot}(E_\gamma) = \frac{N_2}{\mu_2 \rho_2} e^{-\mu_2 \rho_2 z_0} \qquad (4)$$

Thus, the flux of radiation reaching the detector is equal to the radiation from the top-layer and the ground layer minus the amount of absorbed radiation. Mathematically the flux N (Eγ) is equal to:

$$N(E_\gamma) = N_1^{tot}(E_\gamma) + N_2^{tot}(E_\gamma) = \frac{N_1}{\mu_1 \rho_1} + \left(\frac{N_2}{\mu_2 \rho_2} - \frac{N_1}{\mu_1 \rho_1}\right) e^{-\mu_1 \rho_1 z_0} \qquad (5)$$

In FIG. 4, the flux from a radio nuclide is depicted schematically for a top layer which has a higher concentration of that radio nuclide than the soil underneath. The flux as a function of the position in the direction indicated with arrow X shows changes at the positions $x_0$ and $x_1$ due to changes in the thickness of the top layer as is depicted in FIG. 3 at positions $x_0$ and $x_1$. The change in the flux is not proportional to the change in the thickness due to absorption in the pavement layer 301 itself. Hence, as is depicted in FIG. 4, when scanning with the detector over the pavement, at positions $x_{0,1}$ the radiation flux changes. Thus, the thickness of the layer or changes therein may be determined. Application of a method according to the invention to determine the thickness of one or more layers in the pavement is especially suited to determine small changes in the thickness with a relatively large precision because the measured radiation is inversely proportional to the exponent of the thickness.

The accuracy of the determination of the thickness may be increased by determining the contributions of various radio nuclides. For example, the contributions of γ-radiation emitted by $^{40}K$ and the several energies of the γ-radiation emitted by decay products of $^{232}Th$ and of $^{238}U$ may be determined. Since both the absolute concentration and the relative concentrations of these radioactive products differ per layer, the thickness $z_0$ may be derived from a multiple of independent calculations, which increases the accuracy. Determining the contributions of a number of radio nuclides individually also allows to cancel out variations in γ-radiation from the various radio nuclides emitted by material underneath the top layer of which the thickness is to be determined, so that an accurate determination of top layer thickness can be achieved without separate measurement before application of the top layer.

Changes in thickness may be distinguished from changes in composition. Changes in thickness of a layer lead to a reduction or an increase in the flux at the various energy levels of the radionuclides proportional with the specific contributions from the respective radionuclides in that layer. Changes in composition typically lead to other changes in the flux at the various energy levels that are different form changes proportional with the specific contributions from the respective radionuclides in that layer.

The mass-attenuation coefficient μ is hardly dependent on the material and varies gradually and in a known manner with the energy of the γ-radiation.

The precision of the layer thickness measurement may be increased by analyzing the full spectrum or at least energy ranges thereof which contain photo peaks and associated Compton continua. In this way more information provided by the photoelectric effect and the Compton effect is utilized.

As indicated in FIG. 4, changes in the thickness of the top layer cause changes in the intensities of the γ-radiation measured at or above the surface of the pavement. In practice, pavements often consist of several layers, each with a different set of radionuclide concentrations. However, from the principles set forth above, the skilled person will readily be able to formulate adapted algorithms to analyze such multi-layered pavement structures.

According to particular elaboration of the invention, the scintillation crystal is mounted on a car. The car is driven over a road and the scintillation crystal collects γ-radiation from a scanned pavement track along the road as the car drives. With a cycle time of for instance between one and five seconds, received γ-radiation is registered in the form of data representing contributions over the energy spectrum. At 72 km/h, this means that the measured radiation resulting in a spectrum has each time been obtained from a scanned track of 20–100 m. After a length of road has been scanned, the spectra can be compared to identify where changes in the total flux and changes in the relative intensities, i.e. in the shape of the spectra have occurred. Such changes indicate changes in the build-up of the pavement.

Based on the results of this analysis, positions along the road can be identified where samples can be taken that are representative for sections of the road where successive spectra were substantially identical. Furthermore, the results of such analysis can also be used to ensure that calibration samples are taken from the pavement only, or mainly, from sections of the road from which significantly different spectra have been obtained and particularly where the spectra indicate changes in the composition of the pavement material or of the soil underneath, so that an effective contribution to the accuracy of the determination of the property of a layer of the pavement being scanned is obtained from each sample of road pavement.

Thus, the relationship between at least one flux of γ-radiation emitted by the at least one radionuclide and the property of the pavement to be determined can also be established after the γ-radiation measurements have been taken to avoid the need of taking a plurality of samples where no significant changes in the build-up of the pavement are to be found.

In practice it is often only required to check along the length of a freshly paved road whether the thickness of the pavement meets agreed standards. One can then establish reference levels of γ-radiation intensity for one or more energy ranges in the spectrum that are associated to the required thickness of the pavement or pavement layer assuming constant compositions of the road bed and the pavement materials. If the radionuclide concentration responsible for radiation in a certain range of the energy spectrum is higher in the pavement than in the road bed, a radiation intensity in that energy range below the reference level indicates a too thin pavement layer (and vice versa if the concentration of the radionuclide is higher in the road bed). After scanning of the level of γ-radiation along the length of the road, stretches of road where the measurement signal indicates a too thin pavement can easily be identified and, optionally, samples from the pavement can be taken selectively to verify the measurement result.

By separately determining the γ-radiation contributions or concentrations from a number of radio nuclides simultaneously, it is also verified whether the assumption of constant composition of the pavement compound or compounds and the material underneath is valid. If the thickness values calculated from γ-radiation contributions originating from different radionuclides differ from each other more than an acceptable tolerance range, an indication is obtained that the assumption of constant composition of the pavement layer or layers and of the material underneath the pavement is not valid and a new relation between γ-radiation intensities and (required) pavement thickness has to be established.

An example of an application in which the material-composition of the pavement is of interest by itself is when a pavement is to be demolished. Dependent on the material-composition of the pavement different demolition techniques may need to be applied, recycling of the pavement material may be possible or not and the cost of demolition may be different. For instance, if in some sections of a road, the pavement contains polyaromatic carbohydrates which causes the pavement to be unsuitable for recycling whereas other sections are free from such materials, it is of interest for the planning of the demolition where the sections containing polycyclic aromatic hydrocarbon (PAH) are located. Such sections can be identified on the basis of γ-radiation received while scanning the road. Pavement sections containing different materials can be identified directly on the basis of differences in γ-radiation emitted by the different materials to be identified or indirectly on the basis of differences in γ-radiation emitted by other constituents typical for the mixtures containing the materials to be identified. For instance a mixture of bituminous material containing PAH and a filler, such as sand, chalk or furnace slag, can also be identified on the basis of differences between γ-radiation emitted by the fillers associated to different materials containing PAH and not containing PAH.

From the above examples it is apparent that the determination of information regarding a property of the pavement may take various forms. The determination of a property may for instance consist of obtaining an estimate for a value of that property, such as an estimate of the thickness of one or more pavement layers. It may for instance be advantageous to scan the pavement at a low velocity of about 0.5 m/s or lower for providing machine control feedback during road construction. The determination of a property may also consist of merely establishing whether the value of the property is above or below a reference value. The determination of a property may further consist solely in identifying changes in that property, i.e. in establishing whether the value for a property, such as the thickness or the composition, has changed significantly compared with another section of the pavement by comparing the γ-radiation received from a portion of the pavement with the γ-radiation received from another portion of the pavement.

What is claimed is:

1. A method for detecting a property of at least one layer of a pavement, including:
   measuring, in a position above said pavement, at least one flux of radiation received from said pavement and energy levels or at least one range within an energy spectrum of said radiation, said measured radiation including γ-radiation emitted by at least one radio nuclide in or under said pavement; and
   determining information regarding said property from said at least one measured flux and energy levels or at least one range within the energy spectrum of said γ-radiation and predetermined reference data for providing a relationship between at least one flux of γ-radiation of predetermined energy levels or in at least one predetermined energy range and said property.

2. A method according to claim 1, wherein at least one γ-radiation contribution or concentration of at least one individual radio nuclide is determined from said at least one measured flux and energy levels or at least one range within an energy spectrum of said γ-radiation and from said reference data.

3. A method according to claim 2, wherein the radio nuclide is from a group consisting of $^{40}$K, $^{232}$Th, $^{238}$U and decay products of these radionuclides.

4. A method according to claim 3, wherein γ-radiation contributions or concentrations of a plurality of individual radio nuclides are determined.

5. A method according to claim 3, wherein said at least one γ-radiation contribution or concentration is determined by analyzing the energy spectrum of said measured γ-radiation, said reference data including at least one reference spectrum of a reference concentration of an individual radio nuclide.

6. A method according to claim 2, wherein γ-radiation contributions or concentrations of a plurality of individual radio nuclides are determined.

7. A method according to claim 6, wherein said at least one γ-radiation contribution or concentration is determined by analyzing the energy spectrum of said measured γ-radiation, said reference data including at least one reference spectrum of a reference concentration of an individual radio nuclide.

8. A method according to claim 2, wherein said at least one γ-radiation contribution or concentration is determined by analyzing the energy spectrum of said measured γ-radiation, said reference data including at least one reference spectrum of a reference concentration of an individual radio nuclide.

9. A method according to claim 1, wherein said property is the thickness of said at least one layer.

10. A method according to claim 9, wherein said thickness is determined from a difference between the at least one measured flux and at least one reference value for said at least one flux, said at least one reference value being associated to a particular thickness.

11. A method according to claim 1, wherein said property is the composition of said at least one layer.

12. A method according to claim 11, wherein said composition is determined by analyzing the spectrum of said measured radiation and comparing said spectrum with at least one reference spectrum for a pavement compound or constituent.

13. A method according to claim 1, wherein said information is determined by analyzing the spectrum of said measured radiation and comparing said spectrum with at least one reference spectrum for a pavement compound or constituent.

14. A system for detecting a property of a pavement, said system comprising:
- a radiation detector for measuring, in a position above said pavement, at least one flux of radiation received from said pavement and energy levels or at least one range within an energy spectrum of said radiation, said measured radiation including γ-radiation emitted by at least one radio nuclide in or under said pavement;
- a signal processing structure for receiving from said detector a signal representing said at least one measured flux and energy levels or at least one energy range of said measured γ-radiation and for determining information regarding said property from said signal and predetermined reference data for providing a relationship between at least one flux of γ-radiation of predetermined energy levels or in at least one predetermined energy range and said property; and
- an interface for outputting data representing said property.

15. A computer system comprising:
- an interface for inputting data representing at least one measured flux of γ-radiation emitted by at least one radio nuclide in or under a pavement and associated energy levels or at least one associated range within an energy spectrum of said radiation;
- a database containing reference data for providing a relationship between at least one flux of γ-radiation of predetermined energy levels or in at least one predetermined energy range and said property;
- instructions for determining information regarding said property from said reference data in said database and said inputted data; and
- an interface for outputting data representing said property.

16. A computer program on a computer-readable medium for use in a method for detecting a property of at least one layer of a pavement, including:
- instructions for reading inputted data representing at least one measured flux of γ-radiation emitted by at least one radio nuclide in or under a pavement and associated energy levels or at least one associated range within an energy spectrum of said radiation;
- a database containing reference data for providing a relationship between at least one flux of γ-radiation of predetermined energy levels or in at least one predetermined energy range and a property of at least one layer of a pavement from which said γ-radiation is received; and
- instructions for determining information regarding said property from said reference data in said database and said inputted data.

17. A data carrier device including data representing a computer program according to claim 16.

* * * * *